United States Patent [19]

Rajster et al.

[11] Patent Number: 5,040,770

[45] Date of Patent: Aug. 20, 1991

[54] DEVICE FOR TRANSFORMING A LAMINAR FLUID FLOW INTO DROPS

[76] Inventors: Vojko Rajster, Ljuba Sercerja 2, Domzale, Yugoslavia, 61230; Ales Rajster, Brilejeva 14, Ljubljana, Yugoslavia, 61000

[21] Appl. No.: 447,058

[22] Filed: Dec. 7, 1989

[30] Foreign Application Priority Data

Dec. 14, 1988 [YU] Yugoslavia ............................ 2260/88

[51] Int. Cl.⁵ .............................................. F16K 47/12
[52] U.S. Cl. .................................... 251/125; 251/126; 251/205; 138/43
[58] Field of Search ...................... 251/125, 126, 205; 138/41, 42, 43

[56] References Cited

U.S. PATENT DOCUMENTS

| | | | |
|---|---|---|---|
| 880,087 | 2/1908 | Lusebrink | 251/126 X |
| 1,763,687 | 6/1930 | Chadwick et al. | 251/126 X |
| 3,323,774 | 6/1967 | Wilson | 251/125 X |
| 3,880,401 | 4/1975 | Wiltse | 251/205 |
| 3,907,249 | 9/1975 | Persson | 251/126 |
| 4,004,613 | 1/1977 | Purton et al. | 138/42 X |
| 4,044,991 | 8/1977 | Waller | 138/43 X |
| 4,177,947 | 12/1979 | Menzel | 251/126 X |
| 4,634,434 | 1/1987 | Marino, Jr. et al. | 251/126 X |
| 4,653,695 | 3/1987 | Eckstein | 251/126 X |

*Primary Examiner*—John Rivell
*Attorney, Agent, or Firm*—Fleit, Jacobson, Cohn, Price, Holman & Stern

[57] ABSTRACT

A device for transforming a laminar fluid flow into drops, especially infusion fluids, comprises an inlet unit tightly placed into an intermediate unit. A cylinder of the inlet unit is, on its outer circumference, provided with a screw-shaped channel extending from a through-hole leading perpendicularly to the cylinder at its first side to the area of passage of the cylinder into a bottom at its second side. A step projecting radially inwards from the cylinder comprises, on its inner circumference, a number of longitudinally running grooves connected to a number of radially running grooves arranged on a flange of the intermediate unit. A levelling nut is screwed on a thread of a socket comprising a sealing screen which, with a transition fit, is placed between the cylinder of the inlet unit and the cylinder of the intermediate unit. The number of drops per unit of time is adjusted by the rotating of the levelling nut, whereby a longer or a shorter screw-shaped channel 16 and, consequently, an accurate predetermined number of drops, is achieved.

3 Claims, 1 Drawing Sheet

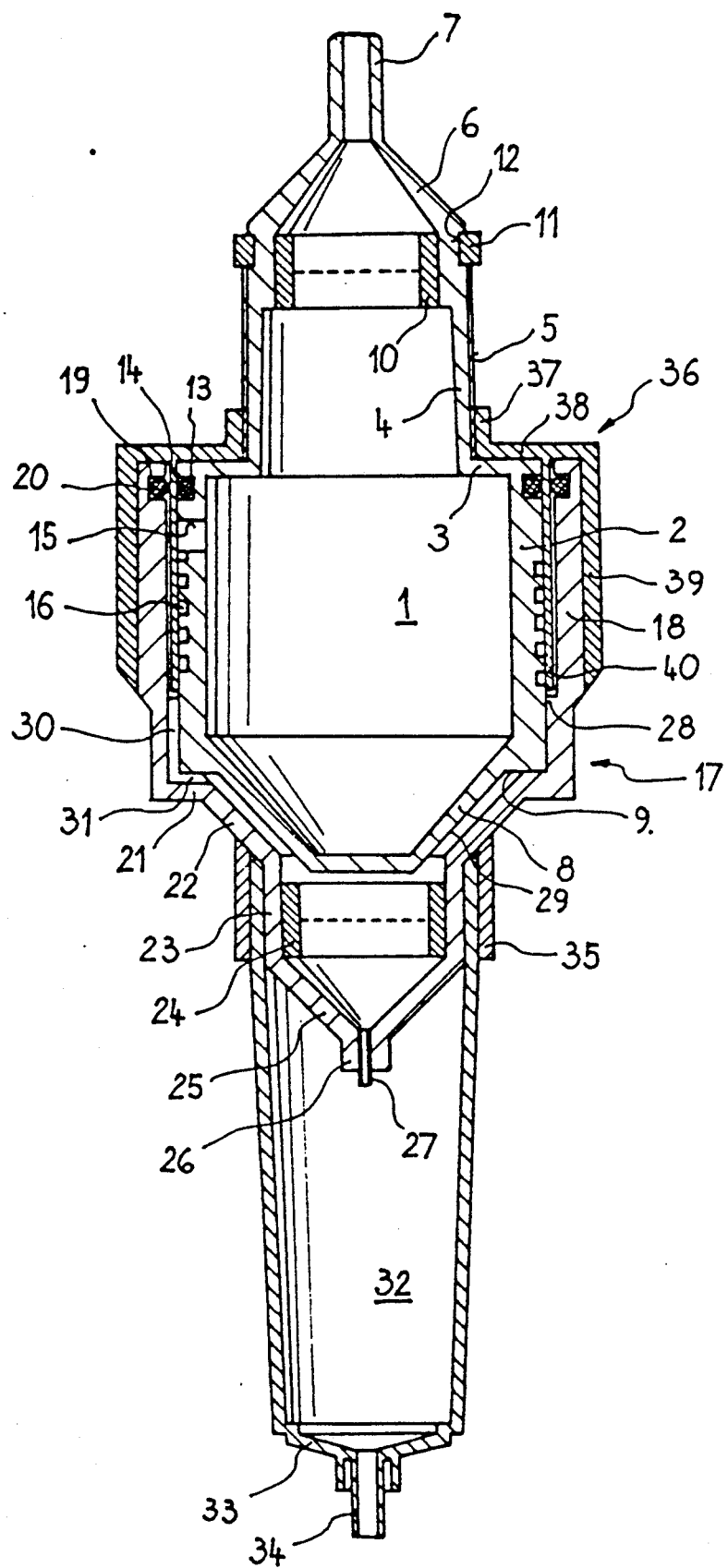

DEVICE FOR TRANSFORMING A LAMINAR FLUID FLOW INTO DROPS

The invention relates to a device for transforming a laminar fluid flow into drops, especially infusion fluids, comprising an oblong cylindrical casing, with a first face at which there is arranged a supply pipe connection, at an opposite side of the casing there is arranged a discharge pipe connection. An adjustable throttling member is located in the casing itself.

A device with the above-mentioned features is known from a leaflet of the Boehringer company, Ingelheim, W. Germany (trade mark INFUCARE). The dropping velocity thereof is adjustable by means of a detachable magnet mounted around the cylindrical casing at the end of the device lying closer to the inlet connection. The magnet acts by means of magnet force on a stem arranged in the cylindrical casing, whereat the stem closes or opens the passageway to a greater or smaller degree.

A drawback of this device is that an external power supply is required to accomplish adjusting of the number of drops. In the given case, the magnet force of a permanent magnet is required, with an intensity which weakens in time. Additionally there are also electromagnetic forces from the surroundings which can act on the stem.

Another drawback is that a continuous manual control of the number of drops is necessary when an extremely small quantity of the fluid is flowing, i.e. below 10 ml/min, and thus an extremely low number of drops per unit of time is in question.

The object of the present invention is to provide a device of the general class discussed in the foregoing which, however, is physically reorganised in such a manner that any continuous manual control of the number of drops, as well as the necessity for additional external power supply to govern the number of drops per unit of time, will be successfully eliminated.

According to the present invention, the object is achieved by means of features described in the characterising clause of claim 1. Further details of the solution according to the invention are described in subclaims.

The invention will now be described on the basis of an example of embodiment with reference to the accompanying drawing, which represents a longitudinal cross-section of the device according to the invention in a closed position.

The device according to the invention comprises an inlet unit 1 consisting of a cylinder 2 having, at its first end, a flange 3 running radially inwards with a socket 4 arranged in the longitudinal direction of the device and provided with an external thread 5 on its entire length. The socket 4 comprises a funnel-shaped extension 6 provided with a supply pipe connection 7. The cylinder 2 has a bottom 8 at its second end, a step 9 being arranged in the area where the bottom 8 passes into the cylinder 2.

Inside the socket 4 there is a fluid strainer 10 placed under the funnel-shaped extension 6. At the outer side of the socket 4 in the area where the socket passes into the extension 6 there is provided a stop ring 11 placed into a corresponding groove 12 on the socket 4. The cylinder 2 has a radially running groove 13 formed on its outside circumference, in which there is placed a seal ring 14. In the area below the seal ring 14 at the side turned towards the bottom 8, there is provided a through-hole 15 leading perpendicularly to the cylinder 2. From the latter towards the bottom 8 there is provided a screw-shaped channel 16 on the outside circumference of the cylinder 2, reaching into the area where the cylinder 2 passes into the bottom 8.

Furthermore, the device according to the invention comprises an intermediate unit 17 consisting of a cylinder 18 having a radially running groove 19 at its upper end in the area of its free edge and from inside, in which there is placed a seal ring 20.

At its lower end, the cylinder 18 has a flange 21 turned perpendicularly inwards, comprising a funnel-shaped part 22, which changes over into a socket 23 having a fluid strainer 24. The socket 23 ends with a funnel-shaped part 25 comprising a socket 26, wherein there is tightly arranged a dropping tube 27. The cylinder 18 of the unit 17 is, at its inner side and in the area of the flange 21, formed with a step 28 projecting radially inwards, which serves as a spacer between the cylinder 18 of the unit 17 and the inlet unit 1 tightly arranged therein; its cylinder 2 is integral with the flange 21 of the unit 17 by means of a step 9. Moreover, each time the distance 29 is formed between the bottom 8 of the unit 1 and the funnel-shaped part 22 of the unit 17. The step 28 comprises a number of longitudinally running grooves 30 on its inner circumference connected onto a number of radially running grooves 31, which are arranged on the flange 21.

Onto the socket 23 there is tightly slipped-on a conical collector 32 which has a bottom 33 with a discharge pipe connection 34 at its end that is averted from the socket 23. The collector 32 is protected against slipping off the socket 23 by means of a thrust ring 35.

Onto the socket 4 of the unit 1 having a thread 5 there is screwed on a levelling nut 36 comprising a thread collar 37 and a radially outwards running plane segment 38, whichs originates from the collar 37 and comprises a mantle 39 running perpendicularly thereto and close to the cylinder 18 of the unit 17. In the direction radially inwards from the mantle 39, the levelling nut 36 has a cylindric sealing screen 40 running in the longitudinal direction of the device; when the device according to the invention is assembled said screen is placed with transition fit between the cylinder 2 of the unit 1 and the cylinder 18 of the unit 17, i.e. into the clearance provided between the cylinder 2 and the cylinder 18 by means of the step 28. Moreover, the fit between the screen 40 and the cylinder 2 is tighter than the fit between the screen 40 and the cylinder 18, and the screen 40 itself in its closed position stretches in the longitudinal direction into the area of the step 28 whereby the channel 16 is completely overlapped.

The device according to the invention operates in the following manner.

The fluid flows inside the unit 1 through the supply pipe connection 7 and the fluid strainer 10. In the closed position shown in the drawing, the sealing screen 40 overlaps the screw-shaped channel 16 over its entire length and the flow is prevented. When unscrewing the levelling nut 36, the latter moves towards the stop ring 11, the channel 16 becomes free and the fluid begins to flow through the hole 15. The fluid glides through the channel 16 due to capillarity and continues its way in the grooves 30, 31, through the strainer 24 and the dropping tube 27 into the collector 32 and out of it through the discharge pipe connection 34.

The amount of the fluid flowing out and the number of drops per unit of time, respectively, are controlled by means of rotating of the nut 36, whereby a longer or a shorter screw-shaped channel 16 and, consequently, an accurate predetermined number of drops is achieved.

To achieve the optimum gliding of the fluid, the channel 16 is dimensioned in such a manner that its entire length to its free-space sectional area for the flow of e.g. 1.5 ml/h of the infusion fluid is in the proportion of 56000:1 for 5% solution, 40000:1 for 10% solution, 30000:1 for 20% solution and 25000:1 for 40% solution. It became evident when testing blood that for the same amount, i.e. 1.5 ml/h, the entire length of the channel 16 to the free-space sectional area is in the proportion of 22000:1.

What is claimed is:

1. A device for transforming a laminar fluid flow into drops, comprising:
    an oblong cylindrical casing having, at one side, a first face at which there is arranged a supply pipe connection and, at an opposite side, a discharge pipe connection,
    an adjustable throttling member located in the cylindrical casing itself,
    a first cylinder of an inlet unit including a screw-shaped channel on its outside circumference, said screw-shaped channel stretching from a through-hole leading perpendicularly to the first cylinder at its first side to an area of passage of the first cylinder into a bottom of the inlet unit at its second side,
    an intermediate unit in which the inlet unit is tightly placed, said intermediate unit having a funnel-shaped part, the inlet and intermediate units being mutually spaced apart by the width of a step projecting radially inwards from a second cylinder of the intermediate unit, so that a distance is formed between the bottom of the inlet unit and said funnel-shaped part of the intermediate unit, the step, on its inner circumference, comprising a number of longitudinally running grooves connected to a number of radially running grooves arranged on a flange of the intermediate unit, and
    a levelling nut screwed on a threaded socket of the inlet unit.

2. A device according to claim 1, wherein the levelling nut comprises a cylindrical sealing screen, directed radially inwards and running in the longitudinal direction of said device, said levelling nut being placed, with a transition fit, between the first cylinder of the inlet unit and the second cylinder of the intermediate unit.

3. A device according to claim 2, wherein the fit between the cylindrical sealing screen and the first cylinder of the inlet unit is tighter than the fit between the cylindrical sealing screen and the second cylinder of the intermediate unit.

* * * * *